United States Patent
Okura et al.

(10) Patent No.: US 6,329,321 B2
(45) Date of Patent: *Dec. 11, 2001

(54) LAWN COLORANT COMPOSITION HAVING REARING EFFECTS

(75) Inventors: Ken Okura; Toshio Hattori; Masayoshi Sakakibara; Shigeo Sasaki, all of Tokyo (JP)

(73) Assignee: Dainichiseika Color & Chemicals Mfg. Co., Ltd, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/488,750

(22) Filed: Jan. 21, 2000

(51) Int. Cl.$^7$ ............... A01N 59/16; C09C 1/22
(52) U.S. Cl. ............... 504/187; 71/31; 106/458
(58) Field of Search ............... 106/301.6, 458; 252/301.16; 71/31; 504/187

(56) References Cited

U.S. PATENT DOCUMENTS

| | | | | |
|---|---|---|---|---|
| 2,911,157 | * | 11/1959 | Converse | 239/287 |
| 4,047,921 | * | 9/1977 | Mues et al. | 71/11 |
| 5,977,029 | * | 11/1999 | Fischer et al. | 504/292 |

FOREIGN PATENT DOCUMENTS

| | | | |
|---|---|---|---|
| B-82034781 | | 7/1982 | (JP) . |
| 1-4677 | * | 1/1989 | (JP) . |
| 1-157904 | * | 6/1989 | (JP) . |
| 03221576 | | 9/1991 | (JP) . |
| 4-314769 | * | 11/1992 | (JP) . |

OTHER PUBLICATIONS

Hona et al. (CA 112:142779, abstract of JP 01219723), 1989.*
Crumbliss et al. (CA 99:202297, abstract of Inorg. Chem. (1983), 22(24), 3541–8), 1989.*
Kuwahara et al. (CA 82:100218, abstract of JP 49093413), 1989.*

* cited by examiner

*Primary Examiner*—S. Mark Clardy
(74) *Attorney, Agent, or Firm*—Oblon, Spivak, McClelland, Maier & Neustadt, P.C.

(57) ABSTRACT

A lawn colorant composition having rearing effects contains a pigment and an adhesive for the pigment. The pigment comprises a blue pigment composed as a primary component of a compound represented by the following formula: $MFe[Fe(CN)_6]$ wherein M represents an alkali metal atom or an ammonium group, one of the two Fe atoms is a divalent ion, and the other Fe atom is a trivalent ion. The adhesive comprises a water-dispersed polymer and a water-soluble polymer having compatibility with said water-dispersed polymer.

13 Claims, No Drawings

LAWN COLORANT COMPOSITION HAVING REARING EFFECTS

BACKGROUND OF THE INVENTION a) Field of the Invention

This invention relates to a colorant composition for lawns, and more specifically to a colorant composition which contains as a primary component a colorant effective not only for coloring lawns but also for promoting growth of the lawns and preventing aging of the lawns and which, when applied to color the lawns, the color so applied can remain for a long time and does not stain other articles through rubbing.

b) Description of Related Art

As lawns wither into a yellow or light brown color in-winter, colorant compositions with green or blue pigments contained therein have conventionally been sprayed to keep the lawns look green.

In these colorant compositions, organic pigments and/or dyes such as copper phthalocyanine blue pigments and copper phthalocyanine green pigments have been employed for the purpose of coloring alone.

These conventionally-employed pigments and dyes are however intended merely to color lawns at their surfaces, and no physiological effects for plants are observed on their coloring components themselves.

In these conventional colorant compositions, emulsions of acrylate ester resins, vinyl acetate resins, ethylene-vinyl acetate resins or the like or emulsions of water-dispersible polymers, such as synthetic rubber latexes, are also used as adhesives for fixing coloring components on turfgrass.

Incidentally, an emulsion of a polymer generally cannot form polymer films at temperatures lower than its film-forming temperature, so that a coloring component, especially a pigment cannot be fixed on turfgrass. When a colorant is sprayed in winter, the temperature is often so low that films cannot be formed with a pigment enclosed therein unless a polymer the lowest film-forming temperature of which is lower than the surrounding temperature, or example, is 5° C. or lower is used.

In general, a polymer the lowest film-forming temperature of which is low is still soft and tacky even after formation into films, and is hence accompanied by a potential problem that they may be rubbed to stain shoes and clothing or at golf courses, to stain equipments such as balls and clubs.

With a view to improving the film-formability of aqueous emulsion polymers at low temperatures, film-forming aids are therefore often used in combination. Illustrative of film-forming aids are alkyl ethers and phenyl ethers of glycols and acetates of such ethers, and benzene or naphthalene solvents containing hydrocarbon groups. These film-forming aids cause no problem when employed industrially, but they are not suited for being sprayed over nature-oriented objects such as lawns and moreover, are also accompanied by a problem from the standpoint of odor.

SUMMARY OF THE INVENTION

The present inventors have proceeded with an extensive investigation with a view to overcoming the drawback that, when lawns are colored with conventional colorant compositions at low temperatures, the colorant compositions are rubbed to stain golf balls and golf equipments and hence with a view to developing a lawn colorant composition the colorant of which acts not only to achieve coloring but also to exhibit physiological effects (growth-promoting and anti-aging effects) for the plant. As a result, it was found that the above object can be achieved by using, as an adhesive, a water-dispersed resin and a water-soluble resin in combination and also a coloring composition containing a specific blue pigment as a coloring component. Based on this finding, the present invention has now been completed.

To achieve the above-described object, the present invention provides a lawn colorant composition having rearing effects, said lawn colorant composition being composed of a pigment and an adhesive therefor, wherein the pigment comprises a blue pigment composed as a primary component of a compound represented by the following formula: $MFe[Fe(CN)_6]$ wherein M represents an alkali metal atom or an ammonium group, one of the two Fe atoms is a divalent ion, and the other Fe atom is a trivalent ion; and the adhesive comprises a water-dispersed polymer and a water-soluble polymer having compatibility with the water-dispersed polymer.

Even when the lawn colorant composition according to the present invention as sprayed over a lawn is rubbed at a low temperature as a result of its contact with an object, the lawn colorant composition does not stain the object. Moreover, the lawn colorant composition can achieve not only coloring of the lawn but also promotion of growth of the lawn and prevention of aging of the lawn.

DETAILED DESCRIPTION OF THE INVENTION AND PREFERRED EMBODIMENTS

The present invention will next be described in further detail by preferred embodiments.

The blue pigment for use in the present invention is a pigment which comprises, as a primary component, a compound represented by the formula: $MFe[Fe(CN)_6]$, and its preferred average particle size ranges from 0.03 to 0.20 $\mu$m, more preferably from 0.05 to 0.10 $\mu$m.

In the above formula, M represents an alkali metal atom, such as sodium or potassium, or an ammonium group, and one of the two Fe atoms is a divalent ion, and the other Fe atom is a trivalent ion.

The coloring component in the colorant composition according to the present invention may be composed solely of a pigment which comprises as a primary component the compound represented by the above formula. To an extent not impairing the object of the present invention, however, another inorganic pigment or an organic pigment or dye may also be used in combination.

The colorant composition according to the present invention is characterized in that it comprises the above-described coloring component and an adhesive and the adhesive is composed of a water-dispersed polymer and a water-soluble polymer.

Preferred examples of the water-dispersed polymer for use in the present invention can include polymer emulsions (or latexes) the lowest film-forming temperatures of which are in a range of from 0 to 100° C., for example, vinyl acetate emulsion, vinyl acetate copolymer emulsions, acrylate ester polymer emulsions, acrylate ester copolymer emulsions, methacrylate ester polymer emulsions, methacrylate ester copolymer emulsions, and styrene copolymer emulsions. More preferred are synthetic resin emulsions the lowest film-forming temperatures of which are in a range of from 0 to 50° C.

Examples of the water-soluble polymer for use in the present invention can include those having compatibility with the water-dispersed polymer, such as polyvinyl alcohol, acrylic acid polymers, acrylic acid copolymers, maleic acid resins, cellulose resins, starch, and chitosan.

The preferred proportion of the water-soluble polymer is in a range of from 1 to 30%, with a range of from 1 to 10 wt. % being more preferred, both based on the water-dispersed polymer (solid content).

When the colorant composition according to the present invention is stored over a long time, it is effective to use one or more of various surfactants as a dispersant for the pigment. From anionic surfactants, cationic surfactants and non-ionic surfactants, one or more surfactants can be selected for use in the present invention in view of the dispersibility of the pigment and also their compatibility with the water-dispersed polymer and water-soluble polymer. Non-ionic surfactants can be mentioned as particularly preferred surfactants, although the present invention is not limited to the use of such non-ionic surfactant or surfactants. Further, defoaming agents, antiseptics, fungicides and the like can also be added as needed.

Next, the present invention will be specifically described by Examples and Comparative Examples. It shall however be borne in mind that the present invention is not limited by the Examples. All designations of "part" or "parts" and "%" in the Examples are by weight.

EXAMPLE 1

Ten (10) parts of a Prussian blue ("Milori Blue 671", trade name; product of Dainichiseika Color & Chemicals Mfg. Co., Ltd.), 10 parts of a disazo yellow AAOA ("Seika Fast Yellow 2400", trade name; product of Dainichiseika Color & Chemicals Mfg. Co., Ltd.), 0.5 part of an anionic surfactant ("Demol EP", trade name; product of Kao Corporation), 4.0 parts of a non-ionic surfactant ("Emulgen A-90", trade name; product of Kao Corporation), and 75.5 parts of water were dispersed in a beads mill. To the resultant dispersion, 10 parts of a water-soluble polymer ("Jullimer AT-210", trade name; product of Nihon Junyaku Co., Ltd.) were evenly mixed, followed by the addition of 120 parts of a water-dispersed polymer ("Boncoat 2310", trade name; product of Dainippon Ink & Chemicals, Incorporated), whereby a lawn colorant composition according to the present invention was obtained.

On October 30 Korai turfgrass lots were sprayed at 300 ml/m$^2$ with 50-fold and 100-fold dilute solutions of the thus-obtained colorant composition, respectively, and their subsequent conditions were observed. The results will be shown in comparison with those of Comparative Example 1 to be described below.

Comparative Example 1

Five (5) parts of a cyanine green ("Cyanine Green 2GN", trade name; product of Dainichiseika Color & Chemicals Mfg. Co., Ltd.), 10 parts of a disazo yellow AAOA ("Seika Fast Yellow 2400", trade name; product of Dainichiseika Color & Chemicals Mfg. Co., Ltd.), 5 parts of an anionic surfactant ("Demol EP", trade name; product of Kao Corporation), and 80 parts of water were dispersed in a beads mill. To the resultant dispersion, 120 parts of a water-dispersed polymer ("Boncoat 2310", trade name; product of Dainippon Ink & Chemicals, Incorporated) were added, whereby a lawn colorant composition of a comparative example was obtained. On October 30 Korai turfgrass lots were sprayed at 300 ml/m$^2$ with 50-fold and 100-fold dilute solutions of the thus-obtained colorant composition, respectively, and their subsequent conditions were observed.

Comparison in the Effects of Spraying

Shortly after the spraying, no substantial difference was observed on coloring ability between Example 1 and Comparative Example 1. The turfgrass lots presented external appearances which were commensurate with the colorant concentrations.

Thirty days after the spraying, that is, on November 29, the aboveground leaves of the unsprayed turfgrass mostly withered into a brown color. The turfgrass sprayed with the colorant composition of Example 1 retained a green color, whereas the turfgrass sprayed with the colorant composition of Comparative Example 1 faded and presented a color close to a withered lawn color. As a result of detailed observation of their conditions, the aboveground parts of the turfgrass in the unsprayed lot and the lots sprayed with the lawn colorant composition of Comparative Example 1 were observed to be in a resting period and to have withered mostly, while in the lots sprayed with the lawn colorant composition of Example 1, the aboveground parts of the turfgrass presented a green color as if they were still active, and adhesion of the colorant on the surfaces of the turfgrass was observed. On the second day after the spraying, the turfgrass in each lot was rubbed with a sheet of white paper to determine a degree of stain. Substantial stain was observed in the case of the lawn colorant composition of Comparative Example 1, but practically no stain was observed in the case of the lawn colorant composition of Example 1.

EXAMPLE 2

Ten (10) parts of a Prussian blue ("N650 Prussian Blue", trade name; product of Dainichiseika Color & Chemicals Mfg. Co., Ltd.), 10 parts of a disazo yellow AAOA ("Seika Fast Yellow 2400", trade name; product of Dainichiseika Color & Chemicals Mfg. Co., Ltd.), 1 part of an anionic surfactant ("Demol N", trade name; product of Kao Corporation), 5 parts of a non-ionic surfactant ("Emulgen A-90", trade name; product of Kao Corporation), 0.2 part of a defoaming agent ("Nopco NXZ", trade name; product of San Nopco Limited), and 73 parts of water were dispersed in a beads mill. To the resultant dispersion, 20 parts of a water-soluble polymer ("Water Sol S-701", trade name; product of Dainippon Ink & Chemicals, Incorporated) and 100 parts of a water-dispersed polymer ("Movinyl 123E", trade name; product of Hoechst Synthesis) were added, whereby a lawn colorant composition according to the present invention was obtained.

Korai turfgrass planted on May 30 in planters were sprayed at 250 ml/m$^2$ with 50-fold and 100-fold dilute solutions of the thus-obtained colorant composition, respectively, and the subsequent growth conditions of the turfgrass planted in the rearing planters were observed. The results will be shown in comparison with those of Comparative Example 2 to be described below.

Comparative Example 2

Five (5) parts of a cyanine blue ("Cyanine Blue 4920", trade name; product of Dainichiseika Color & Chemicals Mfg. Co., Ltd.), 10 parts of a disazo yellow AAOA ("Seika Fast Yellow 2400", trade name; product of Dainichiseika Color & Chemicals Mfg. Co., Ltd.), 5 parts of an anionic surfactant ("Demol N", trade name; product of Kao Corporation), 1 part of a non-ionic surfactant ("Emulgen A-90", trade name; product of Kao Corporation), 1 part of a defoaming agent ("Nopco NXZ", trade name; product of San Nopco Limited), and 78 parts of water were dispersed in a beads mill. To the resultant dispersion, 100 parts of a water-dispersed polymer ("Movinyl 123E", trade name; product of Hoechst Synthesis) were added, whereby a green colorant composition of a comparative example was obtained.

Korai turfgrass planted on May 30 in planters were sprayed at 250 ml/m$^2$ with 50-fold and 100-fold dilute solutions of the thus-obtained colorant composition, respectively, and their subsequent conditions were observed.

Comparison in the Effects of Spraying

Shortly after the spraying, no substantial difference was observed on coloring ability between Example 2 and Comparative Example 2. The turfgrass presented external appearances which were commensurate with the colorant concentrations.

Sixty days after the spraying, that is, on July 31, however, the unsprayed turfgrass did not sufficiently take root, and one third of the entire ground surface was exposed. The turfgrass sprayed with the lawn colorant composition of Example 2 took root completely, and the growth of their aboveground parts was also vigorous.

EXAMPLE 3

Ten (10) parts of a Prussian blue ("N650 Prussian Blue", trade name; product of Dainichiseika Color & Chemicals Mfg. Co., Ltd.), 10 parts of a disazo yellow AAOA ("Seika Fast Yellow 2400", trade name; product of Dainichiseika Color & Chemicals Mfg. Co., Ltd.), 1 part of an anionic surfactant ("Demol N", trade name; product of Kao Corporation), 5 parts of a non-ionic surfactant ("Emulgen A-90", trade name; product of Kao Corporation), 0.2 part of a defoaming agent ("Nopco NXZ", trade name; product of San Nopco Limited), and 73 parts of water were dispersed in a beads mill. To the resultant dispersion, 5 parts of a water-soluble polymer ("Water Sol S-753", trade name; product of Dainippon Ink & Chemicals, Incorporated), 80 parts of a water-dispersed polymer ("Polysol EVA AD-6", trade name; product of Showa Highpolymer Co., Ltd.) and 50 parts of an aqueous solution of chitosan ("Daichitosan W-100", product of Dainichiseika Color & Chemicals Mfg. Co., Ltd.) were added, whereby a lawn colorant composition according to the present invention was obtained.

Comparative Example 3

Three (3) parts of a cyanine blue ("Cyanine Blue 4920", trade name; product of Dainichiseika Color & Chemicals Mfg. Co., Ltd.), 2 parts of a cyanine green ("Cyanine Green 2GN", product of Dainichiseika Color & Chemicals Mfg. Co., Ltd.), 10 parts of a disazo yellow AAMX ("Seika Fast Yellow 2600", trade name; product of Dainichiseika Color & Chemicals Mfg. Co., Ltd.), 5 parts of an anionic surfactant ("Demol N", trade name; product of Kao Corporation), 1 part of a non-ionic surfactant ("Emulgen A-90", trade name; product of Kao Corporation), 1 part of a defoaming agent ("Nopco NXZ", trade name; product of San Nopco Limited), and 78 parts of water were dispersed in a beads mill. To the resultant dispersion, 100 parts of a water-dispersed polymer ("Polysol EVA AD-6" trade name; product of Showa Highpolymer Co., Ltd.) were added, whereby a green colorant composition of a comparative example was obtained.

On October 30 Korai turfgrass lots were sprayed at 300 ml/m$^2$ with 50-fold and 100-fold dilute solutions of the thus-obtained colorant compositions of Example 3 and Comparative Example 3, respectively, and their subsequent conditions were observed.

Comparison in the Effects of Spraying

Shortly after the spraying, no substantial difference was observed on coloring ability between Example 3 and Comparative Example 3. The turfgrass lots presented external appearances which were commensurate with the colorant concentrations.

Thirty days after the spraying, that is, on November 29, the aboveground leaves of the unsprayed turfgrass mostly withered into a brown color. The turfgrass sprayed with the colorant composition of Example 3 retained a green color, whereas the turfgrass sprayed with the colorant composition of Comparative Example 3 faded and presented a color close to a withered lawn color. As a result of detailed observation of their conditions, the aboveground parts of the turfgrass in the unsprayed lot and the lots sprayed with the lawn colorant composition of Comparative Example 3 were observed to be in a resting period and to have withered mostly, while in the lots sprayed with the lawn colorant composition of Example 3, the aboveground parts of the turfgrass presented a green color as if they were still active, and adhesion of the colorant on the surfaces of the turfgrass was observed. On the second day after the spraying, the turfgrass in each lot was rubbed with a sheet of white paper to determine a degree of stain. Substantial stain was observed in the case of the lawn colorant composition of Comparative Example 3, but practically no stain was observed in the case of the lawn colorant composition of Example 3.

What is claimed is:

1. A lawn colorant composition having rearing effects, said lawn colorant composition comprising a pigment and an adhesive therefor, wherein said pigment comprises a blue pigment comprising as a primary component a compound represented by the following formula: MFe[Fe(CN)$_6$] wherein M represents an alkali metal atom or an ammonium group, one of said two Fe atoms is a divalent ion, and the other Fe atom is a trivalent ion; and said adhesive comprises a water-dispersed polymer and a water-soluble polymer, wherein the water-soluble polymer is selected from the group consisting of polyvinyl alcohol, acrylic acid polymers, acrylic acid copolymers, and maleic acid resins.

2. A lawn colorant composition according to claim 1, which additionally contains a yellow dye or pigment.

3. A lawn colorant composition according to claim 1, wherein the water-dispersed polymer is present as a polymer emulsion or latex the lowest film-forming temperature of which is in the range of from 0–100° C.

4. A lawn colorant composition according to claim 3, wherein the polymer emulsion is selected from the group consisting of emulsions of vinyl acetate, vinyl acetate copolymers, acrylate ester polymers, acrylate ester copolymers, methacrylate ester polymers, methacrylate ester copolymers, and styrene copolymers.

5. A lawn colorant composition according to claim 1, wherein said water-soluble polymer is contained in a proportion of from 1 to 30 wt.% based on said water-dispersed polymer.

6. A lawn colorant composition according to claim 5 wherein the water-dispersed polymer is present as a polymer emulsion or latex the lowest film-forming temperature of which is in the range of from 0–100° C.

7. A lawn colorant composition according to claim 6, wherein the polymer emulsion is selected from the group consisting of emulsions of vinyl acetate, vinyl acetate copolymers, acrylate ester polymers, acrylate ester copolymers, methacrylate ester polymers, methacrylate ester copolymers, and styrene copolymers.

8. A lawn colorant composition according to claim 1, which additionally contains at least one surfactant.

9. A lawn colorant composition according to claim 8, which additionally contains a yellow dye or pigment.

10. A lawn colorant composition according to claim 8, wherein the at least one surfactant is a nonionic surfactant.

11. A lawn colorant composition according to claim 10, which additionally contains a yellow dye or pigment.

12. A lawn colorant composition according to claim 8, wherein the at least one surfactant is a nonionic surfactant and an anionic surfactant.

13. A lawn colorant composition according to claim 12, which additionally contains a yellow dye or pigment.

* * * * *